(12) United States Patent
Neumann

(10) Patent No.: US 11,862,322 B2
(45) Date of Patent: Jan. 2, 2024

(54) SYSTEM AND METHOD FOR GENERATING A DYNAMIC WEIGHTED COMBINATION

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/106,658

(22) Filed: Nov. 30, 2020

(65) Prior Publication Data
US 2022/0172819 A1 Jun. 2, 2022

(51) Int. Cl.
| | | |
|---|---|---|
| G16H 20/60 | (2018.01) | |
| G06N 20/00 | (2019.01) | |
| G06F 3/0482 | (2013.01) | |
| G06F 3/01 | (2006.01) | |

(52) U.S. Cl.
CPC .......... G16H 20/60 (2018.01); G06F 3/011 (2013.01); G06F 3/0482 (2013.01); G06N 20/00 (2019.01)

(58) Field of Classification Search
CPC ........ G16H 20/60; G16H 50/80; G16H 10/60; G16H 40/40; G16H 50/20; G06F 3/0482; G06F 3/011; G06F 19/30; G06F 19/32; G06F 19/34; G06F 19/36; G06Q 50/22; G06Q 50/24; G06N 20/00
See application file for complete search history.

(56) References Cited

U.S. PATENT DOCUMENTS

| | | | |
|---|---|---|---|
| 8,560,334 | B2 | 10/2013 | Pertti |
| 8,764,447 | B2 | 4/2014 | Fieldberg |
| 8,924,239 | B1 | 12/2014 | Kurple |
| (Continued) | | | |

FOREIGN PATENT DOCUMENTS

JP 2021064306 A * 4/2021

OTHER PUBLICATIONS

Khan, Asmabee, et al; Optimizing Nutrition using Machine Learning Algorithmsa Comparative Analysis; 2019; International Conference on Nascent Technologies in Engineering (Year: 2019).*

(Continued)

*Primary Examiner* — Peter H Choi
*Assistant Examiner* — Shyam M Goswami
(74) *Attorney, Agent, or Firm* — Caldwell Intellectual Property Law

(57) ABSTRACT

A system and method for generating a dynamic weighted combination includes a computing device configured to gain a nourishment metric, determine a nourishment vector as a function of the nourishment metric, generate a nourishment programs relating to a plurality of aliments as a function of the nourishment vector, determine a quantitative signature as a function of the nourishment programs, and generate a dynamic weighted combination as a function of the quantitative signature, wherein generating further comprises identifying, for each dynamic weighted combination, a degree of refinement according to the refinement criterion, comparing the degree of refinement for each dynamic weighted combination to the degree of refinement for at least one other dynamic weighted combination, and generate a dynamic weighted combination as a function of the comparison.

20 Claims, 6 Drawing Sheets

(56) References Cited

U.S. PATENT DOCUMENTS

| | | |
|---|---|---|
| 9,011,153 B2 | 4/2015 | Bennett et al. |
| 10,043,590 B2 | 8/2018 | Karvela et al. |
| 10,319,477 B1 | 6/2019 | Bill |
| 10,360,495 B2 | 7/2019 | Chapela et al. |
| 10,510,265 B2 | 12/2019 | Jiao et al. |
| 2006/0045909 A1 | 3/2006 | Friesen et al. |
| 2006/0200320 A1 | 9/2006 | Al-Murrani |
| 2007/0260481 A1 | 11/2007 | Marshall |
| 2009/0275002 A1 | 11/2009 | Hoggle |
| 2013/0224694 A1 | 8/2013 | Moore |
| 2015/0269865 A1 | 9/2015 | Volach |
| 2017/0316352 A1 | 11/2017 | Abujbara |
| 2018/0075199 A1 | 3/2018 | Meyerson et al. |
| 2018/0082139 A1 | 3/2018 | Li et al. |
| 2018/0232689 A1* | 8/2018 | Minvielle .............. G06N 5/003 |
| 2018/0233223 A1 | 8/2018 | Solari |
| 2018/0240359 A1* | 8/2018 | Hujsak .................. G06N 5/022 |
| 2018/0293638 A1 | 10/2018 | Simpson |
| 2019/0005201 A1 | 1/2019 | Fleming et al. |
| 2019/0290172 A1 | 9/2019 | Hadad et al. |
| 2019/0304000 A1 | 10/2019 | Simpson |

OTHER PUBLICATIONS https://www.nytimes.com/2019/03/02/opinion/sunday/diet-artificial-intelligence-diabetes.html; By: Eric Topol; Date Mar. 9, 2019; Title: The A.I. Diet.
My diet clinic; Nutrigenomi; http://mydietclinic.com/services/nutrigenomix-testing/#.XP_9bchKg2w; Title: My Diet.
Baze; True change comes from within; https://www.baze.com/.
Select the right plan for your goal; https://www.insidetracker.com/store.

* cited by examiner

SYSTEM AND METHOD FOR GENERATING A DYNAMIC WEIGHTED COMBINATION

FIELD OF THE INVENTION

The present invention generally relates to the field of artificial intelligence. In particular, the present invention is directed to a system and method for generating a dynamic weighted combination.

BACKGROUND

Efficient calculations of nutritional programs are often prevented due to the lack of data being available. Furthermore, even when data is present that accounts for extraneous circumstances, improper algorithms are utilized. This is further complicated by a lack of uniformity of nutritional programs, which results in dissatisfaction of individuals.

SUMMARY OF THE DISCLOSURE

In an aspect a system for generating a dynamic weighted combination, the system comprising a computing device, the computing device configured to gain at least a nourishment metric, determine at least a nourishment vector as a function of the nourishment metric, generate a plurality of nourishment programs relating to a plurality of aliments as a function of the nourishment vector, determine a quantitative signature as a function of the plurality of nourishment programs, and generate a dynamic weighted combination of a plurality of dynamic weighted combinations as a function of the quantitative signature, wherein generating further comprises identifying, for each dynamic weighted combination of the plurality of dynamic weighted combinations, a degree of refinement according to the at least a refinement criterion, comparing the degree of refinement for each dynamic weighted combination of the plurality of dynamic weighted combinations to the degree of refinement for at least one other dynamic weighted combination of the plurality of dynamic weighted combinations, and generate a dynamic weighted combination as a function of the comparison.

In another aspect a method for generating a dynamic weighted combination, the method comprising gaining, by a computing device, at least a nourishment metric, determining, by the computing device, at least a nourishment vector as a function of the nourishment metric, generating, by the computing device, a plurality of nourishment programs relating to a plurality of aliments as a function of the nourishment vector, determining, by the computing device, a quantitative signature as a function of the plurality of nourishment programs, and generating, by the computing device, a dynamic weighted combination of a plurality of dynamic weighted combinations as a function of the quantitative signature, wherein generating further comprises identifying, for each dynamic weighted combination of the plurality of dynamic weighted combinations, a degree of refinement according to the at least a refinement criterion, comparing the degree of refinement for each dynamic weighted combination of the plurality of dynamic weighted combinations to the degree of refinement for at least one other dynamic weighted combination of the plurality of dynamic weighted combinations, and generate a dynamic weighted combination as a function of the comparison.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a dynamic weighted combination. In an embodiment, the disclosure may determine at least a nourishment vector as a function of a nourishment metric. Aspects of the present disclosure can be used to generate a plurality of nourishment programs relating to a plurality of aliments. Aspects of the present disclosure can also be used to determine a quantitative signature as a function of the plurality of nourishment programs. Aspects of the present disclosure allow for generating a dynamic weighted combination of a plurality of dynamic weighted combinations as a function of the quantitative signature. Exemplary embodiments illustrating aspects of the present disclosure are described below in the context of several specific examples.

Figure 1:
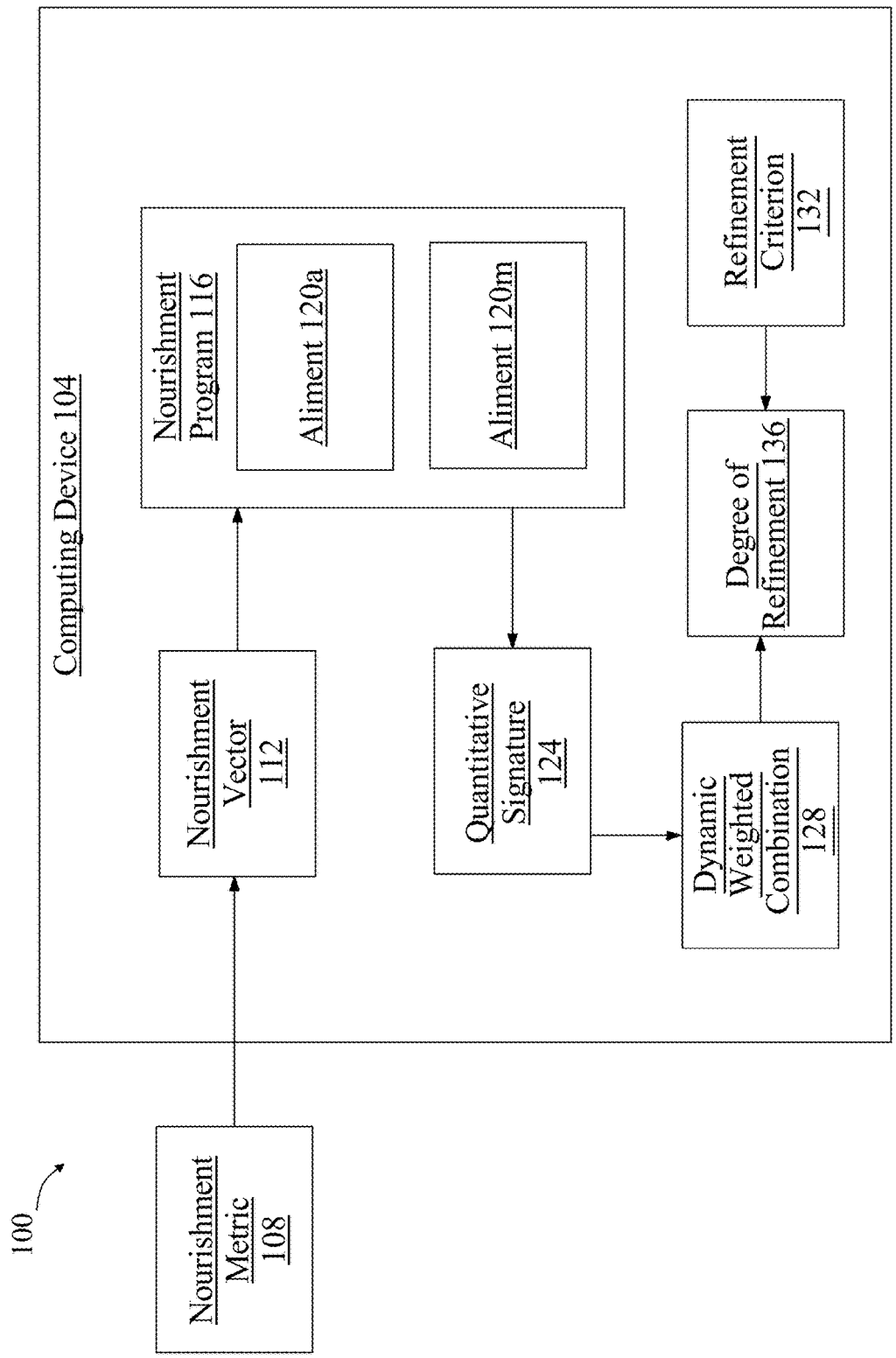
FIG. 1 is a block diagram illustrating an exemplary embodiment of a system for generating a dynamic weighted combination.

Referring now to FIG. 1, an exemplary embodiment of a system 100 for generating a dynamic weighted combination is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to gain at least a nourishment metric 108. As used in this disclosure a "nourishment metric" is an element of data relating to a user nutrient, wherein a user nutrient is comprised of one or more qualitative elements that may indicate the current health status of a user. For example, nourishment metric 108 may include, without limitation, a biological extraction. A "biological extraction" as used in this disclosure includes at least an element of user biological data. As used in this disclosure, "biological data" is data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, biological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various nourishments such as dehydration, nutrient deficiencies, anemia, and/or blood loss. Biological extraction data may alternatively or additionally include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Nourishment metric 108 may be gained as a function of one or more monitoring inputs, wherein a monitoring input is an input from an external source that relates to a user health status, as described below in reference to FIG. 2.

Still referring to FIG. 1, computing device 104 determines at least a nourishment vector 112 as a function of nourishment metric 108. As used in this disclosure "nourishment vector" is a vector that relates to the user nutrients. As used in this disclosure "vector" as defined in this disclosure is a data structure that represents one or more quantitative values and/or measures user nutrients. A vector may be represented as an n-tuple of values, where n may be at least a value and/or two or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where a is attribute number i of the vector. Scaling and/or normalization may function to make vector comparison independent of absolute quantities of attributes, while preserving any dependency on similarity of attributes. As a non-limiting example nourishment vector 112 may be 12 as a function of a biological extraction that identifies low iron levels in an individual. As a further non-limiting example nourishment vector 112 may be as a that identifies lethargy due to reduced sleep and decreased caffeine consumption.

Still referring to FIG. 1, computing device 104 may determine nourishment vector 112 by gaining at least a nourishment element from at least a nourishment directory, wherein a nourishment directory is a database of nutrients as described below in detail, in reference to FIG. 3. As used in this disclosure a "nourishment element" is a nutrient and/or nourishment category that relates to one or more nutrients. As used in this disclosure a "nutrient" is a substance and/or consumable that produces a source of energy to an organism such that the organism may survive, grow, and/or reproduce. As a non-limiting example a nourishment element may consist of macronutrients and/or micronutrients. As used in this disclosure "macronutrients" are a chemical class of compounds that individuals consume in large quantities to provide the individual with the bulk of energy. Macronutrients may include, without limitation carbohydrates, such as glucose, sucrose, ribose, amylose, amylopectin, maltose, galactose, fructose, lactose, and the like thereof. Macronutrients may include, without limitation proteins, such as standard amino acids, wherein standard amino acids include, but are not limited to, alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine, valine, and the like thereof. Macronutrients may include without limitation fats, such as saturated fatty acids, monounsaturated fatty acids, polyunsaturated fatty acids, essential fatty acids, and the like thereof. As used in this disclosure "micronutrients" are essential elements required by organisms in varying quantities to orchestrate a range of physiologic functions to maintain health. As a non-limiting example, micronutrients may consist of vitamins, wherein vitamins include vitamins A, $B_1$, $B_2$, $B_3$, $B_5$, $B_6$, $B_7$, $B_9$, $B_{12}$, C, D, E, K, and the like thereof. As a further non-limiting example, micronutrients may consist of minerals, such as potassium, chlorine, sodium, calcium, phosphorous, magnesium, iron, zinc, manganese, copper, iodine, chromium, molybdenum, selenium, cobalt, and the like thereof.

With continued reference to FIG. 1, nourishment vector 112 may be determined as a function of the nourishment element and at least a vector-machine-learning model. As used in this disclosure a "vector machine-learning model" is a machine-learning model to produce a nourishment vector output given nourishment elements and nourishment metrics provided as inputs; this is in contrast to a non-machine learning software program where the commands to be executed are determined in advance by a user and written in a programming language. Vector machine-learning model may include one or more vector machine-learning processes such as supervised, unsupervised, or reinforcement machine-learning processes that apparatus 104 and/or a remote device may or may not use in the determination of nourishment vector 112. As used in this disclosure "remote device" is an external device to computing device 104. A vector machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, the vector machine-learning process may be trained as a function of a vector training set. As used in this disclosure a "vector training set" is a training set that correlates at least nourishment element and nourishment metric to a measurable value. For example, and without limitation, nourishment element of a macronutrient consisting of carbohydrates and a nourishment metric of a questionnaire to a measurable value of 33. As a further non-limiting example, a vector training set may relate nourishment element of a micronutrient consisting of minerals and a nourishment metric of a biological extraction to a measurable value of 71. The vector training set may be received as a function of user-entered valuations of nourishment elements, nourishment metrics, and/or measurable values. The vector training set may be received by one or more past iterations of the previous nourishment vectors. The vector training set may be received by one or more remote devices that at least correlate a nourishment element and nourishment metric to a measurable value, wherein a remote device is an external device to computing device 104.

Still referring to FIG. 1, computing device 104 may receive the vector machine-learning model from the remote device that utilizes one or more vector machine learning processes, wherein a remote device is described above in detail. For example, and without limitation, a remote device may include a computing device, external device, processor, and the like thereof. The remote device may perform the vector machine-learning process using the vector training set to generate nourishment metric 112 and transmit the output to computing device 104. The remote device may transmit a signal, bit, datum, or parameter to computing device 104 that at least relates to nourishment metric 112. Additionally or alternatively, the remote device may provide an updated machine-learning model. For example, and without limitation, an updated machine-learning model may be comprised of a firmware update, a software update, a vector machine-learning process correction, and the like thereof. As a non-limiting example a software update may incorporate a new nourishment metric that relates to a modified nourishment vector. Additionally or alternatively, the updated machine learning model may be transmitted to the remote device, wherein the remote device may replace the vector machine-learning model with the updated machine-learning model and determine the nourishment vector as a function of the nourishment metric using the updated machine-learning model. The updated machine-learning model may be transmitted by the remote device and received by computing device 104 as a software update, firmware update, or corrected vector machine-learning model. For example, and without limitation a vector machine-learning model may utilize a neural net machine-learning process, wherein the updated machine-learning model may incorporate polynomial regression machine-learning process.

With continued reference to FIG. 1, computing device 104 generates a nourishment program 116 of a plurality of nourishment programs as a function of nourishment vector 112. As used in this disclosure a "nourishment program" is a program consisting of aliments that are to be consumed over a given time period, wherein a time period is a temporal measurement such as seconds, minutes, hours, days, weeks, months, years, and the like thereof. Nourishment program 116 recommends at least an aliment 120*a* of a plurality of aliments 120*m*. As used in this disclosure "aliment" is a substance to be consumed to at least sustain an individual. Aliment 120*a-m* may consist of a plant, animal, and/or fungi. As a non-limiting example nourishment program 116 may consist of recommending steak for 3 days. As a further non-limiting example a nourishment program 116 may recommend chicken for a first day, spaghetti for a second day, and mushrooms for a third day. Nourishment program 116 may include one or more diet programs such as paleo, keto, vegan, vegetarian, and the like thereof.

Still referring to FIG. 1, computing device 104 may generate nourishment program 116 by determining at least a nutrient deficiency. As used in this disclosure a "nutrient deficiency" is a deficiency of a nutrient that exists in the user's body. As a non-limiting example, a nutritional deficiency may include vitamin K that is 1 ng/mL, wherein vitamin K should be 100 ng/mL in the user's body. As a further non-limiting example a nutritional deficiency may include glucose that is 20 ng/mL, wherein glucose should be 200 ng/mL in the user's body. Computing device may generate nourishment program 116 using the nutrient deficiency, nourishment vector 112, and at least a nutrient machine-learning model. As used in this disclosure a "nutrient machine-learning model" is a machine-learning model to produce a nourishment program output given nutrient deficiencies and nourishment vectors provided as inputs; this is in contrast to a non-machine learning software program where the commands to be executed are determined in advance by a user and written in a programming language. Nutrient machine-learning model may include one or more nutrient machine-learning processes such as supervised, unsupervised, or reinforcement machine-learning processes that apparatus 104 and/or a remote device may or may not use in the determination of nourishment program 116. A nutrient machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, the nutrient machine-learning process may be trained as a function of a nutrient training set. As used in this disclosure a "nutrient training set" is a training set that correlates at least nutrient deficiency and a nourishment vector to an aliment. For example, and without limitation, a nutrient deficiency of a low vitamin D and a nourishment metric of 2 for vitamin D may relate to an aliment of milk and/or cheese. As a further non-limiting example, a nutrient training set may relate the nutrient deficiency of a decreased potassium and a nourishment metric of 7 for sodium to an aliment of a banana. The nutrient training set may be received as a function of user-entered valuations of nutrient deficiencies, nourishment vectors, and/or aliments. The nutrient training set may be received by one or more past iterations of the previous nourishment programs. The nutrient training set may be received by one or more remote devices that at least correlate a nutrient deficiency and a nourishment vector to an aliment, wherein a remote device is an external device to computing device 104.

Still referring to FIG. 1, computing device 104 may receive the nutrient machine-learning model from the remote device that utilizes one or more nutrient machine learning processes, wherein a remote device is described above in detail. For example, and without limitation, a remote device may include a computing device, external device, processor, and the like thereof. The remote device may perform the nutrient machine-learning process using the nutrient training set to generate nourishment program 116 and transmit the output to computing device 104. The remote device may transmit a signal, bit, datum, or parameter to computing device 104 that at least relates to nourishment program 116. Additionally or alternatively, the remote device may provide an updated machine-learning model. For example, and without limitation, an updated machine-learning model may be comprised of a firmware update, a software update, a nutrient machine-learning process correction, and the like thereof. As a non-limiting example a software update may incorporate a new nutritional deficiency that relates to a modified nourishment program. Additionally or alternatively, the updated machine learning model may be transmitted to the remote device, wherein the remote device may replace the nutrient machine-learning model with the updated machine-learning model and determine the nourishment program using the updated machine-learning model. The updated machine-learning model may be transmitted by the remote device and received by computing device 104 as a software update, firmware update, or corrected nutrient machine-learning model. For example, and without limitation a nutrient machine-learning model may utilize a Naïve Bayes machine-learning process, wherein the updated machine-learning model may incorporate Random Forest machine-learning process.

Still referring to FIG. 1, computing device 104 is configured to determine a quantitative signature 124 as a function of nourishment program 116 of the plurality of nourishment programs. As used in this disclosure "quantitative signature" is a signature relating to an element of cost of nourishment program 116. Quantitative signature 124 may include an element of cost relating to the price of aliment 120*a-m*. As a non-limiting example the price of a pork chop may be $7.99. Quantitative signature 124 may include an element of cost relating to the time of the nourishment program. As a non-limiting example the time associated with the nourishment program may consist of 3 months of expense to the individual. Quantitative signature 124 may include an element of cost relating to the production of aliment 120a-m. As a non-limiting example the cost relating to the energy expenses such as gas, water, electric, and the like thereof may relate to the cost to produce aliment 120a-m. Quantitative signature 124 may include an element of cost relating to the travel expenses in procuring aliment 120a-m. As a non-limiting example, travel to and from a grocery store may result in a cost of $5.32 in fuel and maintenance costs and/or $1.25 for public transportation. Quantitative signature 124 may include an element of cost relating to the costs related to the delivery of aliment 120a-m. As a non-limiting example a delivery cost may be incurred as a fee for a courier or transportation service to deliver aliment 120a-m. Quantitative signature 124 may be generated as a result of one or more aliments relating to one or more nourishment programs. As a non-limiting example quantitative signature 124 may relate to a nourishment program associated with a keto diet as well as a quantitative signature for a vegan diet.

Still referring to FIG. 1, quantitative signature 124 may be determined by gaining at least a geolocation element. As used in this disclosure "geolocation element" is an identification of a real-world geographical location of a user. Geolocation element may be obtained from a radar source, remote device such as a mobile phone, and/or internet connected device location. Geolocation element may include a global positioning system (GPS) of a user. Geolocation element may include geographic coordinates that may specify the latitude and longitude of a particular location where a user is located. Geolocation element may include one or more cell-tower triangulations, wherein a cell-tower triangulation identifies at least an alpha, beta, and gamma sector. Each of the sectors identify one or more distances that an individual may be from the cell-tower. One or more cell-towers may be used in the determination of the geolocation element. For example, and without limitation, a first cell-tower may identify a mobile phone located in sector beta with a distance of 8.4 miles, wherein a second cell-tower may identify the same mobile phone in sector alpha at 23.8 miles. This may be used iteratively until the exact location of the mobile phone, and/or internet connected device may be identified. Geolocation element may include one or more received signal strength indicators (RSSI), wherein a RSSI is a measurement of the power present in a received radio signal. For example, and without limitation, RSSI may include an IEEE 802.11 wireless networking device, wherein the relative received signal strength in the wireless environment is received in arbitrary units, such that a geolocation element may be identified. Quantitative signature 124 may utilize an element of user geolocation to identify one or more prices, costs, and/or expenses associated with nourishment program 116.

With continued reference to FIG. 1, quantitative signature 124 may be determined by selecting a set of aliments as a function of nutritional program 116. As used in this disclosure a "set of aliments" is a category of aliments that at least ameliorate a particular nutritional deficiency. As a non-limiting example a set of aliments associated with high protein may be categorized together. Computing device 104 may generate quantitative signature 124 for a first nourishment program as a function of the set of aliments and at least a temporal element. As used in this disclosure "a temporal element" is an element of data describing a specific time range, wherein a time range may consist of milliseconds, seconds, minutes, hours, days, weeks, months, years, and the like thereof. As a non-limiting example a particular set of aliments may result in a smaller temporal element in amending the nutritional deficiency of decreased phenylalanine in a user's body. As a further non-limiting example a category of aliments consisting of enhancing the amino acid phenylalanine in a suer's body may consist of salmon, steak, pork, chicken, and tofu, wherein each aliment may have a particular quantitative signature associated with the same function.

With continued reference to FIG. 1, computing device 104 is configured to generate a dynamic weighted combination 128 of a plurality of dynamic weighted combinations as a function of quantitative signature 124. As used in this disclosure "dynamic weighted combinations" are weighted and combined values associated with nourishment program 116 as a function of one or more quantitative signatures and at least a refinement criterion 132, wherein each quantitative signature and refinement criterion has an established weighted value and the weighted value is combined with the value of the nourishment program. Dynamic weighted combination 128 may vary as a function of one or more quantitative signatures and at least a refinement criterion and/or dynamic weighted combination 128 may be associated with a specific nourishment program that is a function of one or more quantitative signatures and at least a refinement criterion. Furthermore, a dynamic weighted combination may re-define a magnitude of a weight and/or combination as a function of the refinement criterion As used in this disclosure "refinement criterion" are values and/or ranges of values associated with one or more attributes of a user. Refinement criterion 132 may include at least a nourishment qualifier relating to the user. As used in this disclosure "nourishment qualifier" is a nourishment program that a user wants, wishes, and/or desires to complete. Nourishment qualifier may consist of one or more diet programs and/or nutritional programs such as keto, paleo, vegan, vegetarian, pescatarian, and the like thereof. Refinement criterion 132 may include at least a pecuniary constraint relating to the user. As used in this disclosure "pecuniary constraint" is one or more currency ranges that a user wants, wishes, and/or desires to maintain. Pecuniary constraint may consist of a single aliment threshold, wherein a single aliment may not exceed a specified currency range. Pecuniary constraint may consist of a nutritional program threshold, wherein nutritional program 116 may not exceed a specified currency range. Pecuniary constraint may be selected, wherein a singular aliment cost may be associated with a cost of a single aliment at a single point in time. Pecuniary constraint may be generated as a function of. As a non-limiting example dynamic weighted combination 128 may display a range of quantitative signatures associated with a nutritional program, wherein one or more of the potential nourishment programs recommended may be eliminated as a function of refinement criterion 132.

Still referring to FIG. 1, computing device is configured to generate dynamic weighted combination by identifying a degree of refinement 136 for each dynamic weighted combinations of the plurality of dynamic weighted combinations according to the refinement criterion 132. As used in this disclosure "degree of refinement" is a metric that identifies one or more degrees of freedom from nourishment program 116. As a non-limiting example, degree of refinement 136 may include identifying one or more pecuniary constraints associated with the plurality of nourishment programs. As a further non-limiting example, degree of refinement 136 may identify one or more nourishment qualifiers associated with the plurality of nourishment programs. Computing device 104 may compare degree of refinement 136 for each dynamic weighted combination of the plurality of dynamic weighted combinations to the degree of refinement for at least one other dynamic weighted combination of the plurality of dynamic weighted combinations. Dynamic weighted combination may be generated as a function of the comparison.

Still referring to FIG. 1, computing device 104 may generate the dynamic weighted combination by identifying at least a desired outcome. As used in this disclosure "desired outcome" is one or more achievements that a user may want, wish, and/or desire. As a non-limiting example a desired outcome may be related to losing a particular amount of weight. As a further non-limiting example a desired outcome may be related to increasing overall protein consumption. As a further non-limiting example a desired outcome may be related to a user wanting to lower LDL levels in a user's circulatory system. Computing device 104 may identify desired outcomes by receiving at least a user input from a graphical user interface. As used in this disclosure 'user input" is information received by a user from a graphical user interface pertaining to a desired outcome. As used in this disclosure "graphical user interface" is a form or other graphical element having data entry fields, where a user may select one or more fields to enter one or more elements rating to the desired outcome. Graphical user interface may provide a drop-down menu and display one or more desired outcomes where a user may select one or more elements relating to the desired outcome. Graphical user interface may list one or more categories relating to the desired outcome, such as burn fat, gain muscle, increase health, lower blood pressure, and the like thereof. As a non-limiting example, user input may be received from one or more user devices, such as a smartphone, tablet, computer, and the like thereof. Computing device 104 may determine a program modifier as a function of the desired outcome.

Still referring to FIG. 1, computing device 104 may determine a program modifier as a function of the desired outcome. As used in this disclosure a "program modifier" is a set of degrees of freedom that at least relates to a modification variable associated with a desired outcome, such that the degrees of freedom may modified and/or alter the dynamic weighted combination. Program As a non-limiting example a program modifier may include one or more degrees of freedom associated with a specific modification variable associated with the desired outcome that at least minimizes and/or maximizes the dynamic weighted combination. As a further non-limiting example the a program modifier associated with a variable that increases the weighted value of high protein aliments may be determined as a function of a desired outcome of reduced fat percentage.

Still referring to FIG. 1, computing device 104 may modify the nourishment program as a function of program modifier and generate dynamic weighted combination 128 as a function of the modified nourishment program. Program modifier may modify dynamic weighted combination 128 by altering weighted variables associated with quantitative signatures 124 and refinement criterion 132. For example, and without limitation, program modifier may identify one or more variables associated with reduced meat consumption as a function of a desired outcome, wherein the program modifier is incorporated into the refinement criteria such that an altered weighted dynamic combination is generated. Program modifier may modify one or more weighted values associated with the nourishment program. As a non-limiting example the program modifier may determine a user desired outcome of decreased aliment frequency, wherein the program modifier may increase the weighted value of a nourishment program that is associated with intermittent fasting.

Figure 2:
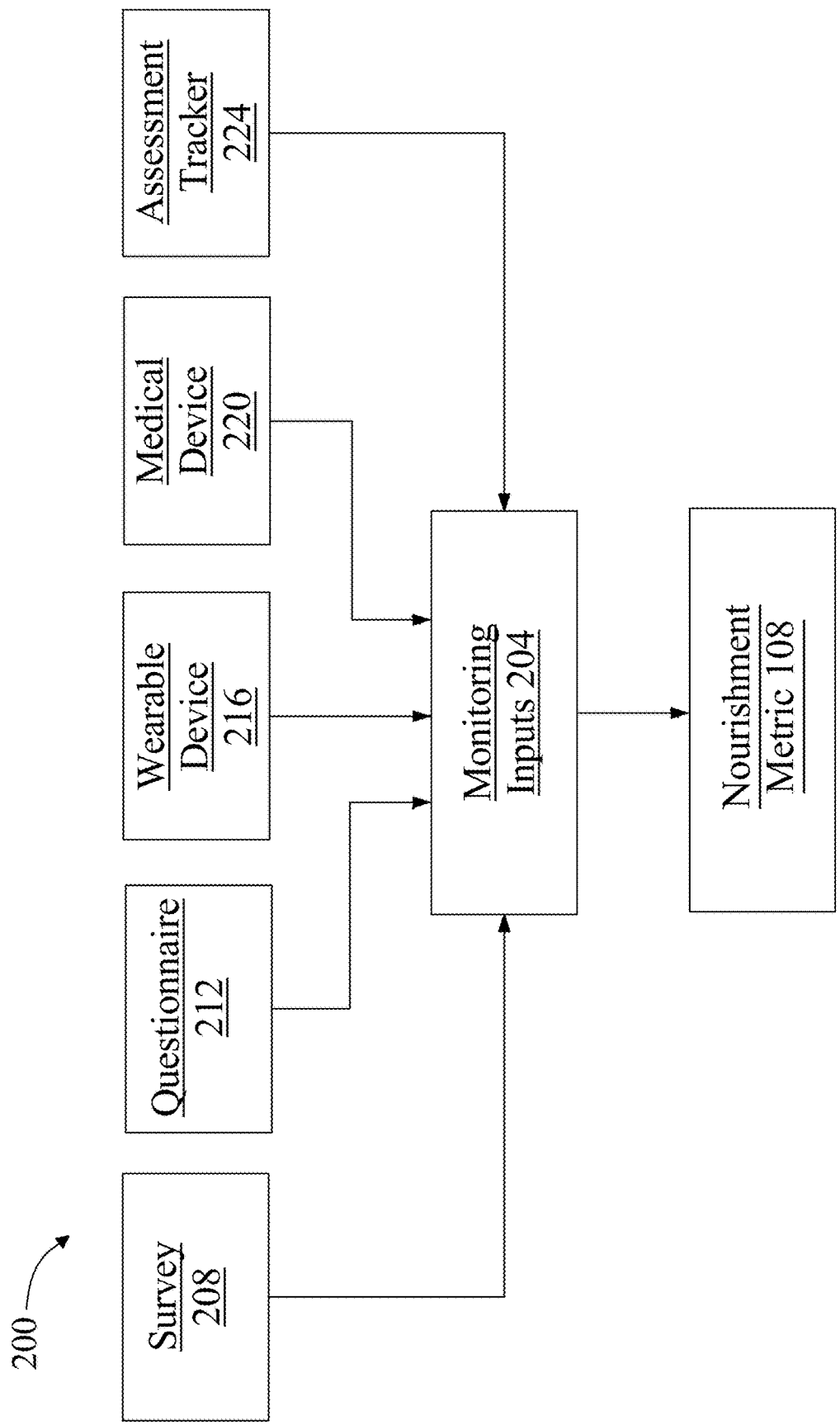
FIG. 2 is a block diagram of an exemplary embodiment of monitoring inputs according to an embodiment of the invention.

Now referring to FIG. 2, an exemplary embodiment of 200 of a monitoring input 204 according to an embodiment of the invention is illustrated. As used in this disclosure "monitoring input" is an input an external source that relates to a user health status. Monitoring input 204 may include data input via a survey 208. As used in this disclosure "survey" is a written or verbal set of questions, wherein the process of collecting, aggregating, and analyzing the responses relates to nourishment metric 108. As a non-limiting example survey 208 may include a verbal set of questions that relate to one or more nutritional deficiencies of a user. Monitoring input 204 may include an external source of a questionnaire 212. As used in this disclosure "questionnaire" is a written set of questions of a plurality of written questions that may indicate one or more nourishment metrics associated with the user. For example, and without limitation, questionnaire 212 may include providing a user with a written form in which the user has to answer about nutritional deficiencies they may be experiencing.

Still referring to FIG. 2, monitoring input 204 may include a signal generated by a wearable device 216. As used in this disclosure "wearable device" is an electronic device that is worn on the person of a user, such as without limitation close to and/or on the surface of the skin, wherein the device can detect, analyze, and transmit nourishment metrics relating to the user. The monitoring device my consist of, without limitation, near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. The monitoring device may include directed light monitoring devices such as spectrophotometric device that at least identifies nourishment metrics such as body mass index, fat percentage, water percentage, bone mass percentage, muscle mass percentage, and the like thereof. The monitoring device may include, without limitation, earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables.

Still referring to FIG. 2, monitoring input 204 may include an external source of a medical device 220. As used in this disclosure "medical device" is a device operated by one or more informed advisors, wherein an informed advisor may include any medical professional who may assist and/or participate in the medical treatment of a user, that relates to one or more biological status's of the user. As a non-limiting example, an informed advisor may include a medical doctor, nurse, physician assistant, pharmacist, yoga instructor, nutritionist, spiritual healer, meditation teacher, fitness coach, health coach, life coach, and the like. As a further non-limiting example, a medical device of may include a/an stethoscope, ultrasound device, MRI device, PET scanner, CT scanner, X-ray device, electrocardiogram device, and the like thereof. Monitoring input 204 may include an external source of an assessment tracker 224. As used in this disclosure "assessment tracker" is data-tracking tool that provides incisive data about one or more nourishment metrics relating to the user. As a non-limiting example assessment tracker 224 may include a program that monitors a user's nutrition over a period of time, such as seconds, minutes, hours, days, months, and/or years. As a further non-limiting example, assessment tracker 224 may include a worksheet that the user may record nourishment metrics to be entered into computing device 104.

Figure 3:
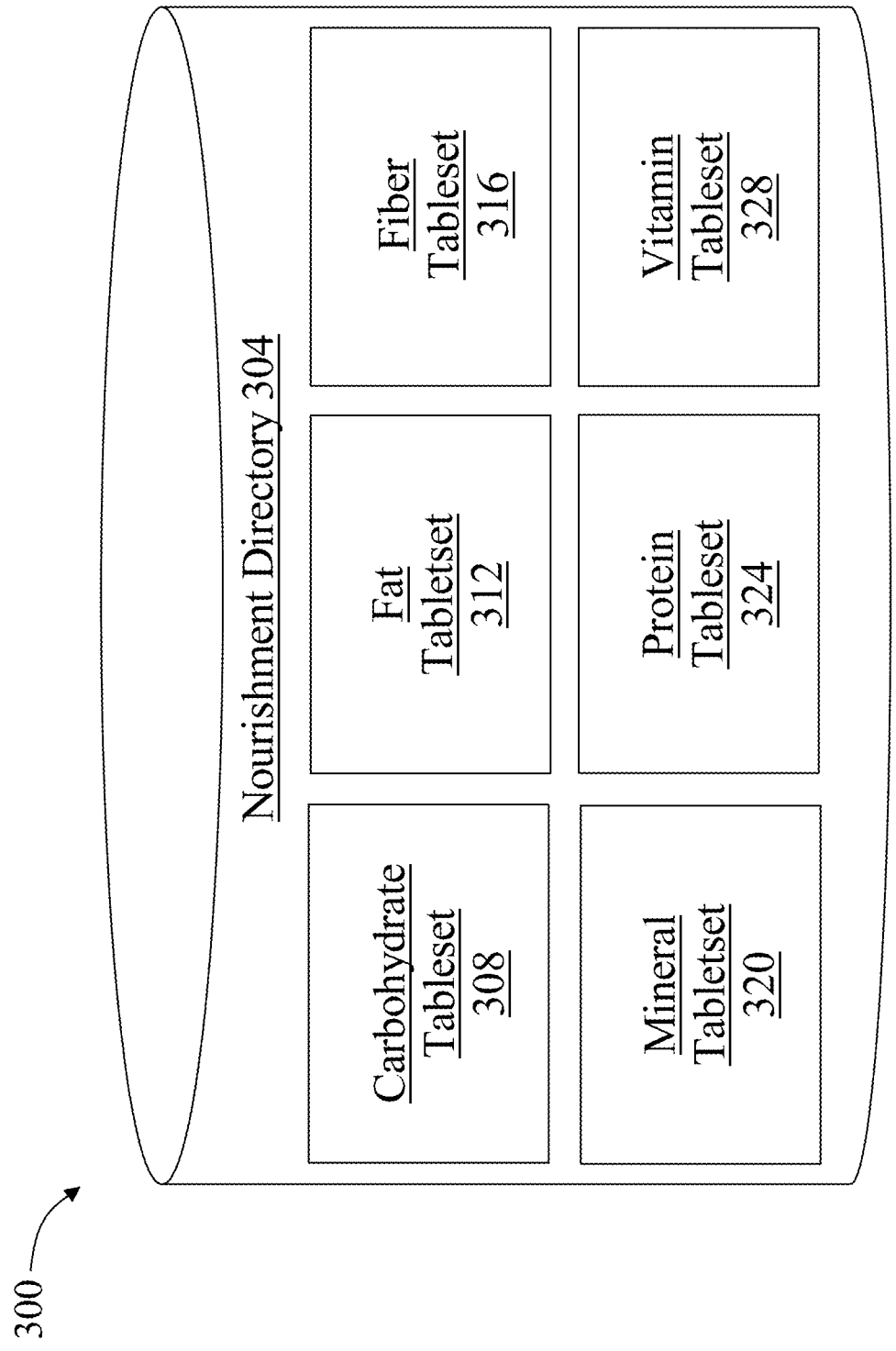
FIG. 3 is a block diagram of an exemplary embodiment of a nourishment directory according to an embodiment of the invention.

Now referring to FIG. 3, an exemplary embodiment 300 of a nourishment directory 304 according to an embodiment of the invention is illustrated. Nourishment directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Nourishment directory 304 may alternatively or additionally be implemented using a distributed data storage protocol and/or data structure, such as a distributed hash table or the like. Nourishment directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Nourishment directory 304 may include a carbohydrate tableset 308. Carbohydrate tableset 308 may relate to types of carbohydrates that at least provide necessary nourishment vectors. As a non-limiting example, carbohydrate tableset 308 may include monosaccharides, disaccharides, oligosaccharides, polysaccharides, and the like thereof. Nourishment directory 304 may include a fat tableset 312. Fat tableset 312 may relate to esterified fatty acids that at least provide necessary nourishment vectors. Fat tableset may include, without limitation, triglycerides, monoglycerides, diglycerides, phospholipids, sterols, waxes, and free fatty acids. Fiber tableset 316 may relate to types of fiber that at least provide necessary nourishment vectors. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Nourishment directory 304 may include a mineral tableset 320. Mineral tableset 320 may relate to types of minerals that at least provide necessary nourishment vectors. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Nourishment directory 304 may include a protein tableset 324. Protein tableset 324 may relate to types of proteins that at least provide necessary nourishment vectors. As a non-limiting example, protein tableset 316 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Nourishment directory 304 may include a vitamin tableset 328. Vitamin tableset 328 may relate to types of vitamins that at least provide necessary nourishment vectors. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
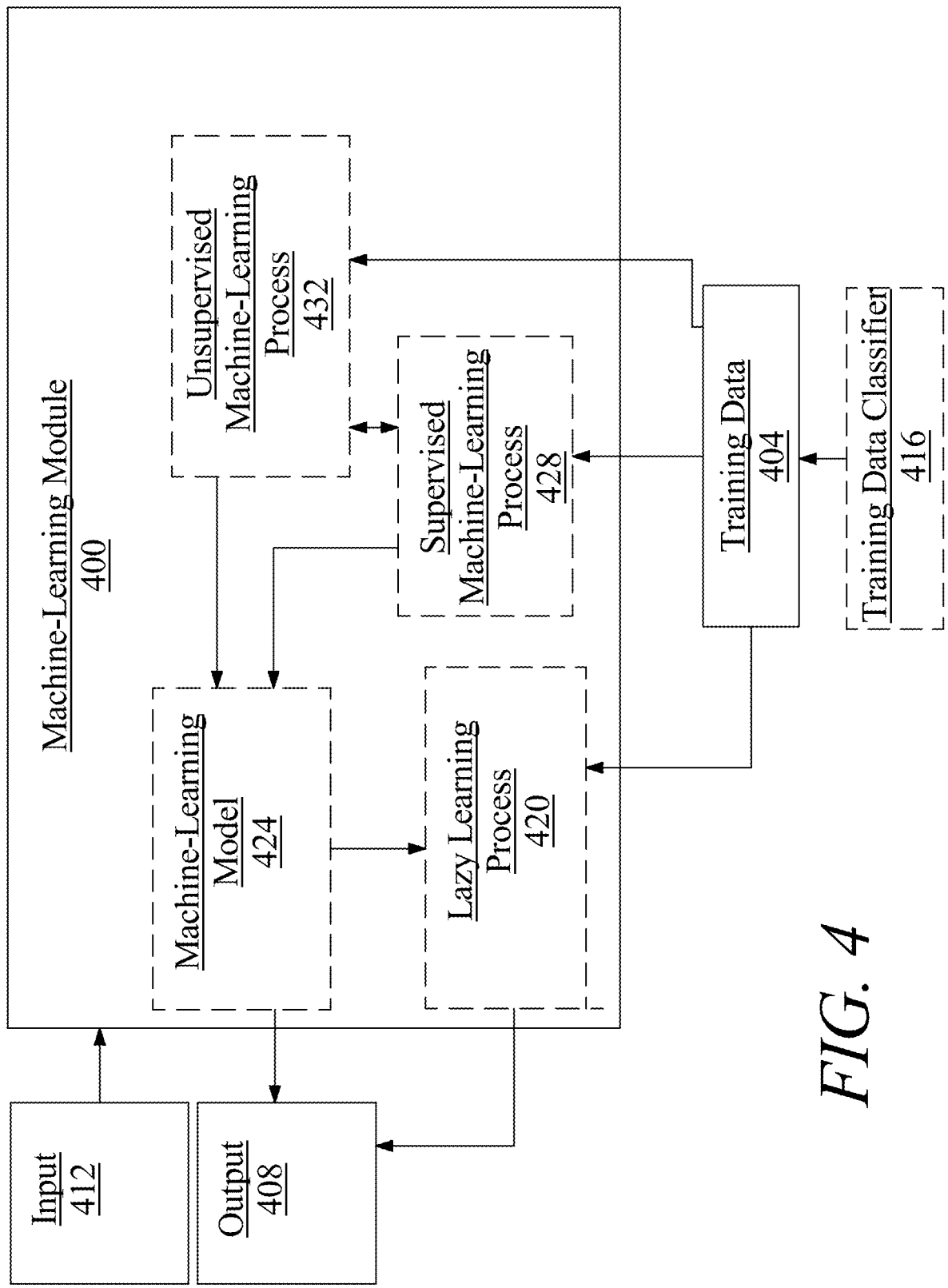
FIG. 4 is a block diagram of an exemplary embodiment of a machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example nutrient deficiencies and nourishment vectors may be inputs, wherein nourishment programs may be generated as outputs.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to specific nutrient deficiencies such as the types of nutrients that exist within the user's body.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include nutrient deficiencies and nourishment vectors as described above as inputs, nourishment programs as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 5:
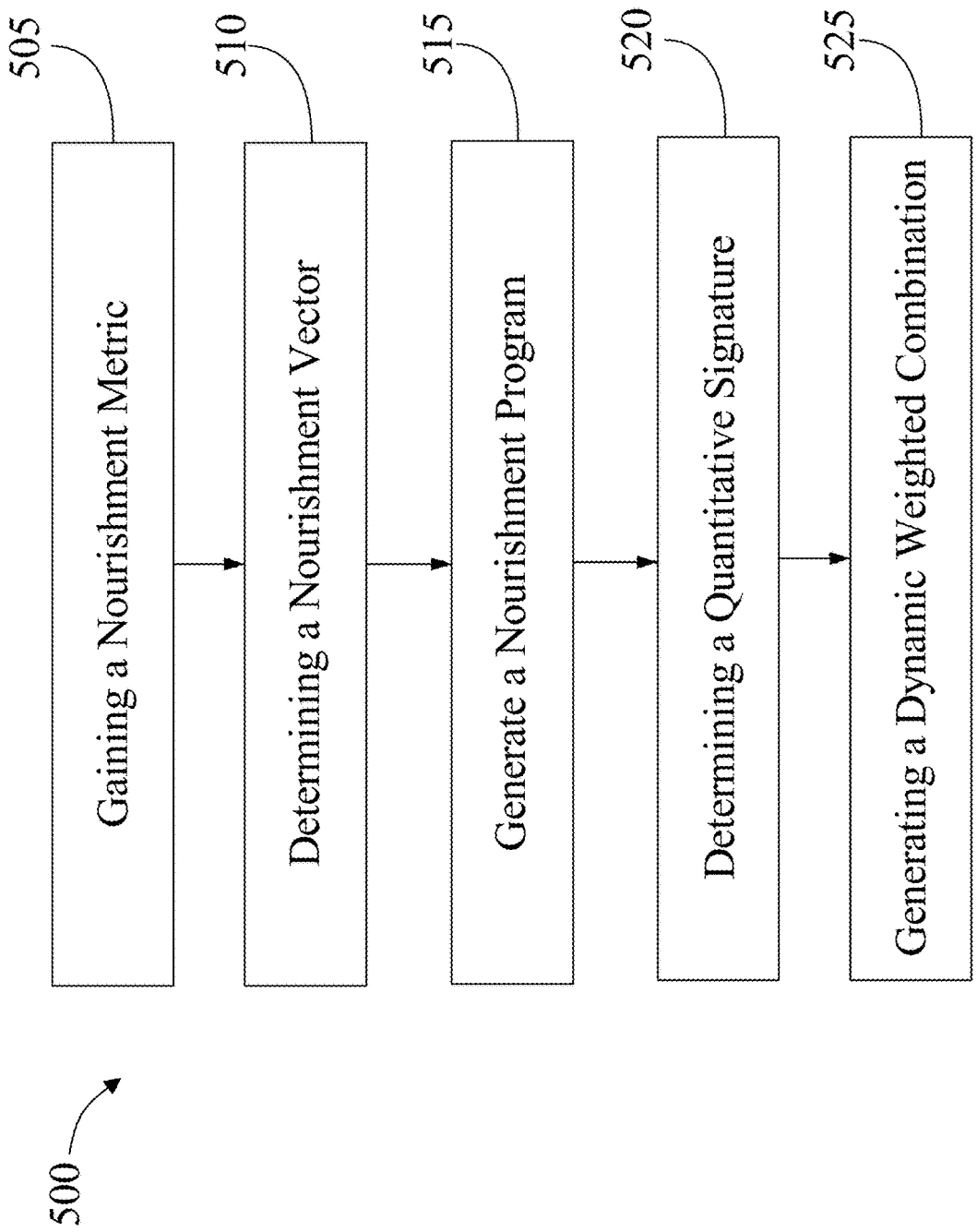
FIG. 5 is a process flow diagram illustrating an exemplary embodiment of a method of generating a dynamic weighted combination.

Now referring to FIG. 5, an exemplary embodiment of a method 500 for generating is illustrated. At step 505, a computing device 104 gains a nourishment metric 108. Computing device 104 includes any of the computing device 104 as described above in reference to FIG. 104. Nourishment metric includes any of the nourishment metric 108 as described above, in reference to FIGS. 1-4. For instance, and without limitation nourishment metric may include any qualitative information relating to a user's health status.

Still referring to FIG. 5, at step 510, computing device 104 determines at least a nourishment vector 112 as a function of nourishment metric 108. Nourishment vector 112 includes any of the nourishment vector as described above, in reference to FIGS. 1-4.

Still referring to FIG. 5, at step 515, computing device 104 generates a nourishment program 116 of a plurality of nourishment programs relating to an aliment 124a of a plurality of aliments 124a-m as a function of nourishment vector 112. Nourishment program 116 includes any of the nourishment program 116 as described above, in reference to FIGS. 1-4. Aliment 124a-m includes any of the aliment 124a-m as described above in reference to FIGS. 1-4.

Still referring to FIG. 5, at step 520, computing device 104 determines a quantitative signature 124 as a function of nourishment program 116. Quantitative signature 124 includes any of the quantitative signature 124 as described above in reference to FIGS. 1-4.

With continued reference to FIG. 5, at step 525, computing device 104 generates a dynamic weighted combination 128 of a plurality of dynamic weighted combinations as a function of quantitative signature 124. Computing device 104 generates dynamic weighted combination 128 identifying a degree of refinement 136 according to a refinement criterion 132. Degree of refinement 136 includes any of the degree of refinement as described above, in reference to FIGS. 1-4. Refinement criterion 132 includes any of the refinement criterion 132 as described above, in reference to FIGS. 1-4. Computing device 104 compares degree of refinement 136 for each dynamic weighted combination of the plurality of weighted combinations to the degree of refinement for at least one other dynamic combination of the plurality of dynamic weighted combinations and generates dynamic weighted combination 128 as a function of the comparison.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
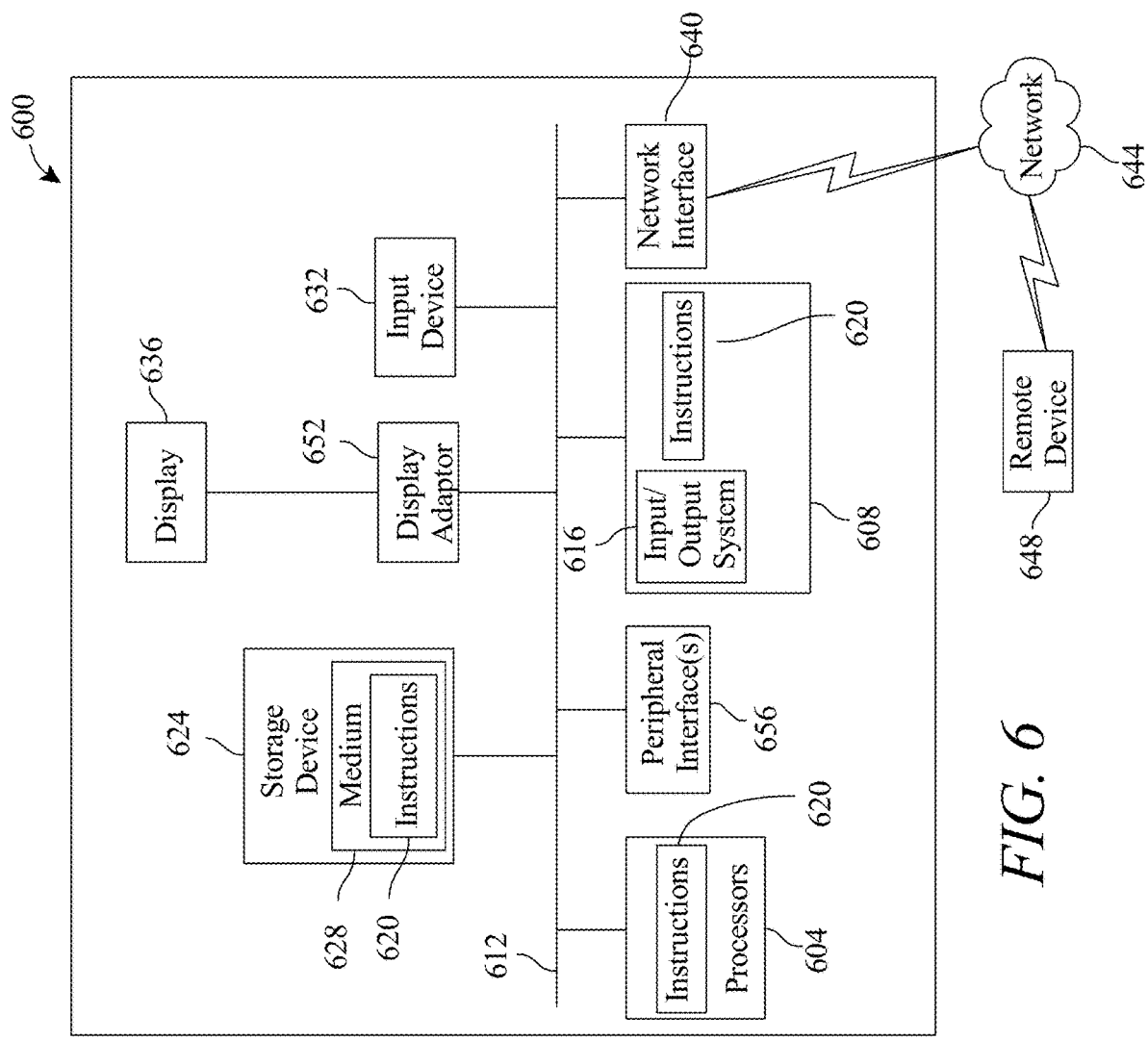
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a dynamic weighted combination, the system comprising a computing device, the computing device configured to:
   gain at least a nourishment element from at least a nourishment directory;
   receive at least a nourishment metric from a user, the at least a nourishment metric comprising a biological extraction, wherein receiving the at least a nourishment metric comprises:
      receiving user responses from the user using questionnaire, the user responses comprising user nutritional deficiencies;
      receiving the at least a nourishment metric from a wearable device configured to detect, analyze and transmit the at least a nourishment metric relating to the user;
   determine at least a nourishment vector from the biological extraction of the user, wherein determining the at least a nourishment vector comprises:
      receiving a vector training set, wherein the vector training set correlates nourishment element data comprising macronutrients and micronutrients and nourishment metric data to at least a nourishment vector value;
      training a vector machine-learning model as a function of the vector training set wherein the vector machine learning model determines a fatty acid deficiency using a deep deterministic policy gradient; and
      determining the at least a nourishment vector as a function of the at least a nourishment element, at least a nourishment metric and the vector machine-learning model, wherein the vector machine learning model inputs the at least a nourishment element and the at least a nourishment metric and outputs the at least a nourishment vector;
         wherein the at least a nourishment vector describes a nourishment value of esterified fatty acids that provide a threshold level of nourishment generate a plurality of nourishment programs relating to a plurality of aliments as a function of the at least a nourishment vector, wherein generating the plurality of nourishment programs comprises:
      receiving a nutrient training set, wherein the nutrient training set correlates nutrient deficiency data and nourishment vector data to aliment data;
      training a nutrient machine-learning model as a function of the nutrient training set;
      generating the plurality of nourishment programs as a function of the nutrient machine-learning model, wherein the nutrient machine-learning model produces a nourishment program output given nutrient deficiencies and the at least a nourishment vector provided as inputs;
   determine a quantitative signature as a function of the plurality of nourishment programs, wherein determining the quantitative signature further comprises:
      selecting a first set of aliments as a function of a first nourishment program;
      determining a user geographical location by cell-tower triangulation of a mobile phone, wherein the cell-tower triangulation comprises identifying an alpha sector, a beta sector, and a gamma sector;
      generating a plurality of elements of cost relating to user travel expenses in procuring each aliment of the first set of aliments as a function of the user geographical location; and
      determining a first quantitative signature for the first nourishment program as a function of the first set of aliments and the plurality of elements of cost; and
   generate a dynamic weighted combination of a plurality of dynamic weighted combinations as a function of the quantitative signature, wherein generating the dynamic weighted combination further comprises:
identifying, for each dynamic weighted combination of the plurality of dynamic weighted combinations, a degree of refinement according to at least a refinement criterion, the degree of refinement indicating at least one degree of freedom of each of the plurality of dynamic weighted combinations based on the refinement criterion;
comparing the degree of refinement for each dynamic weighted combination of the plurality of dynamic weighted combinations to the degree of refinement for at least one other dynamic weighted combination of the plurality of dynamic weighted combinations; and
generating the dynamic weighted combination as a function of the comparison.

2. The system of claim 1, wherein the at least a nourishment metric includes a monitoring input of a plurality of monitoring inputs.

3. The system of claim 1, wherein determining the quantitative signature further comprises gaining at least a geolocation element and determining the quantitative signature as a function of the at least a geolocation element.

4. The system of claim 1, wherein determining the quantitative signature further comprises:
selecting a second set of aliments as a function of a second nourishment program; and
generating a second quantitative signature for the second nourishment program as a function of the second set of aliments and at least a temporal element.

5. The system of claim 1, wherein generating the dynamic weighted combination further comprises:
identifying at least a desired outcome;
determining a program modifier as a function of a desired outcome;
modifying one nourishment program of the plurality of nourishment programs as a function of the program modifier, wherein the program modifier comprises at least a degree of freedom of a specific modification variable associated with the desired outcome that at least minimizes or maximizes the dynamic weighted combination; and
generating the dynamic weighted combination as a function of the modified nourishment program.

6. The system of claim 5, wherein identifying the at least a desired outcome includes receiving at least the user input from a graphical user interface and identifying the at least a desired outcome as a function of the user input.

7. The system of claim 1, wherein the at least a refinement criterion includes at least a nourishment qualifier relating to the user, wherein the degree of refinement identifies the at least a nourishment qualifier including a nourishment program the user desires to complete.

8. The system of claim 1, wherein the at least a refinement criterion includes at least a pecuniary constraint, wherein the at least a pecuniary constraint comprises a currency range the user desires to maintain.

9. A method for generating a dynamic weighted combination, the method comprising:
gaining, by a computing device, at least a nourishment element from at least a nourishment directory;
receiving, at the computing device, at least a nourishment metric from a user, the at least a nourishment metric comprising a biological extraction, wherein receiving the at least a nourishment metric comprises:
receiving user responses from the user using questionnaire, the user responses comprising user nutritional deficiencies;
receiving the at least a nourishment metric from a wearable device configured to detect, analyze and transmit the at least a nourishment metric relating to the user;
determining, by the computing device, at least a nourishment vector from the biological extraction of the user, wherein determining the at least a nourishment vector comprises:
receiving a vector training set, wherein the vector training set correlates nourishment element data comprising macronutrients and micronutrients and nourishment metric data to at least a nourishment vector value;
training a vector machine-learning model as a function of the vector training set wherein the vector machine learning model determines a fatty acid deficiency using a deep deterministic policy gradient;
determining the at least a nourishment vector as a function of the at least a nourishment element, at least a nourishment metric and the vector machine-learning model, wherein the vector machine learning model inputs the at least a nourishment element and the at least a nourishment metric and outputs the at least a nourishment vector;
wherein the at least a nourishment vector describes a nourishment value of esterified fatty acids that provide a threshold level of nourishment;
generating, by the computing device, a plurality of nourishment programs relating to a plurality of aliments as a function of the at least a nourishment vector, wherein generating the plurality of nourishment programs comprises:
receiving a nutrient training set, wherein the nutrient training set correlates nutrient deficiency data and nourishment vector data to aliment data;
training a nutrient machine-learning model as a function of the nutrient training set;
generating the plurality of nourishment programs as a function of the nutrient machine-learning model, wherein the nutrient machine-learning model produces a nourishment program output given nutrient deficiencies and the at least a nourishment vector provided as inputs;
determining, by the computing device, a quantitative signature as a function of the plurality of nourishment programs, wherein determining the quantitative signature further comprises:
selecting a first set of aliments as a function of a first nourishment program;
determining a user geographical location by cell-tower triangulation of a mobile phone, wherein the cell-tower triangulation comprises identifying an alpha sector, a beta sector, and a gamma sector;
generating a plurality of elements of cost relating to user travel expenses in procuring each aliment of the first set of aliments as a function of the user geographical location; and
determining a first quantitative signature for the first nourishment program as a function of the first set of aliments and the plurality of elements of cost; and
generating, by the computing device, a dynamic weighted combination of a plurality of dynamic weighted combinations as a function of the quantitative signature, wherein generating the dynamic weighted combination further comprises:

identifying, for each dynamic weighted combination of the plurality of dynamic weighted combinations, a degree of refinement according to at least a refinement criterion, the degree of refinement indicating at least one degree of freedom of each of the plurality of dynamic weighted combinations based on the refinement criterion;

comparing the degree of refinement for each dynamic weighted combination of the plurality of dynamic weighted combinations to the degree of refinement for at least one other dynamic weighted combination of the plurality of dynamic weighted combinations; and generating the dynamic weighted combination as a function of the comparison.

10. The method of claim 9, wherein the at least a nourishment metric includes a monitoring input of a plurality of monitoring inputs.

11. The method of claim 9, wherein determining the quantitative signature further comprises gaining at least a geolocation element and determining the quantitative signature as a function of the at least a geolocation element.

12. The method of claim 9, wherein determining the quantitative signature further comprises:

selecting a second set of aliments as a function of a second nourishment program; and generating a second quantitative signature for the second nourishment program as a function of the second set of aliments and at least a temporal element.

13. The method of claim 9, wherein generating the dynamic weighted combination further comprises:

identifying at least a desired outcome;

determining a program modifier as a function of a desired outcome;

modifying one nourishment program of the plurality of nourishment programs as a function of the program modifier, wherein the program modifier comprises one or more degrees of freedom associated with a specific modification variable associated with the desired outcome that at least minimizes or maximizes the dynamic weighted combination; and generating the dynamic weighted combination as a function of the modified nourishment program.

14. The method of claim 13, wherein identifying the at least a desired outcome includes receiving at least the user input from a graphical user interface and identifying the at least a desired outcome as a function of the user input.

15. The method of claim 9, wherein the at least a refinement criterion includes at least a nourishment qualifier relating to the user, wherein the degree of refinement identifies the at least a nourishment qualifier including a nourishment program the user desires to complete.

16. The method of claim 9, wherein the at least a refinement criterion includes at least a pecuniary constraint, wherein the at least a pecuniary constraint comprises a currency range the user desires to maintain.

17. The system of claim 1, wherein the at least a nourishment metric is selected from the group consisting essentially of a body mass index, a water percentage, a fat percentage, a bone mass percentage, a muscle mass percentage, and combinations thereof.

18. The method of claim 9, wherein the at least a nourishment metric is selected from the group consisting essentially of a body mass index, a water percentage, a fat percentage, a bone mass percentage, a muscle mass percentage, and combinations thereof.

19. The system of claim 8, wherein the at least a pecuniary constraint further comprises:

a single aliment threshold, wherein a single aliment may not exceed a specified currency range; or a nutritional program threshold, wherein a nutritional program may not exceed a specified currency range.

20. The method of claim 16, wherein the at least a pecuniary constraint further comprises:

a single aliment threshold, wherein a single aliment may not exceed a specified currency range; or a nutritional program threshold, wherein a nutritional program may not exceed a specified currency range.

* * * * *